(12) United States Patent
Molin et al.

(10) Patent No.: US 8,126,555 B2
(45) Date of Patent: Feb. 28, 2012

(54) BIDIRECTIONAL COMMUNICATIONS BETWEEN A GENERATOR AND SENSORS OR ACTUATORS OF A LEAD FOR AN ACTIVE IMPLANTABLE MEDICAL DEVICE

(75) Inventors: Renzo Dal Molin, Chatillon (FR); Karima Amara, Sceaux (FR)

(73) Assignee: ELA Medical S.A.S., Montrouge (FR)

( * ) Notice: Subject to any disclaimer, the term of this patent is extended or adjusted under 35 U.S.C. 154(b) by 408 days.

(21) Appl. No.: 12/359,338

(22) Filed: Jan. 25, 2009

(65) Prior Publication Data

US 2009/0192572 A1 Jul. 30, 2009

(30) Foreign Application Priority Data

Jan. 25, 2008 (FR) .................................. 08 00375

(51) Int. Cl.
*A61N 1/00* (2006.01)
(52) U.S. Cl. ........................................... 607/27; 607/59
(58) Field of Classification Search ................ 607/4–28, 607/59
See application file for complete search history.

(56) References Cited

U.S. PATENT DOCUMENTS

| | | | |
|---|---|---|---|
| 5,304,208 A | 4/1994 | Inguaggiato et al. |
| 5,454,838 A | 10/1995 | Vallana et al. |
| 5,496,351 A | 3/1996 | Plicchi et al. |
| 5,693,075 A | 12/1997 | Plicchi et al. |
| 7,214,189 B2 | 5/2007 | Zdeblick |
| 2003/0149456 A1 | 8/2003 | Rottembourg et al. |
| 2004/0220650 A1 | 11/2004 | Houben et al. |

FOREIGN PATENT DOCUMENTS

| | | |
|---|---|---|
| EP | 0515319 | 11/1992 |
| EP | 0582162 | 2/1994 |
| EP | 0655260 | 5/1995 |
| EP | 1356847 | 10/2003 |
| WO | WO 2006029090 | 3/2006 |

OTHER PUBLICATIONS

Foreign Search Report (Annexe Au Rapport De Recherche Preliminaire; Ralatif A La Demande De Brevet Francais No. FR 0800375 FA 705200), Aug. 26, 2008.

*Primary Examiner* — Scott Getzow
(74) *Attorney, Agent, or Firm* — Orrick Herrington & Sutcliffe, LLP (57) ABSTRACT

An active implantable medical device including bidirectional communications between a generator and sensors or actuators located at the distal extremity of a lead. A lead (14) is connected at its proximal end to a generator (10) and has at the distal end electrodes (38, 42) able to come in contact with surrounding tissues. A two-wire connection (34, 36) connects these electrodes to the generator. The lead incorporates transducers (24, 26) of sensor or actuator type. The generator includes circuits for sending and receiving digital data (46, 48, 50, 54, 56) capable of producing instructions to one of the transducers and to receive and decode information from one of the transducers in response to a specific instruction produced by the generator. The transducer is able to receive, decode and carry out the aforementioned controls, as well as send data in response.

11 Claims, 4 Drawing Sheets

FIG_1

FIG_2

FIG_5

BIDIRECTIONAL COMMUNICATIONS BETWEEN A GENERATOR AND SENSORS OR ACTUATORS OF A LEAD FOR AN ACTIVE IMPLANTABLE MEDICAL DEVICE

FIELD OF THE INVENTION

The present invention relates to "active medical devices" as defined by Directive 93/42/CEE of Jun. 14, 1993 of the Council of the European Communities, and more particularly to "active implantable medical devices" as defined by Directive 90/385/CEE of the Council of the European Communities. This definition includes with its scope devices that monitor cardiac activity and deliver impulses of stimulation, re-synchronization, defibrillation and/or cardioversion in the event of a cardiac rhythm disorder detected by the device, and also neurological devices, cochlear implants, etc., as well as devices for the measurement of pH or intra-corporeal impedance (such as devices that measure a trans-pulmonary impedance or an intra-cardiac impedance).

BACKGROUND OF THE INVENTION

Implantable medical devices typically comprise a case that is generally referred to as a "generator," electrically and mechanically connected to one or more "leads" that are in turn provided with electrodes intended to come in contact with the tissues to be stimulated by delivering an impulse (or pulse) and/or detected by sensing (or collecting) an electric signal: myocardium, nerve, muscle . . . etc. In the case of an implantable medical device for therapy, these electrodes can be intracardiac electrodes (placed in a cavity of the myocardium in contact with the intra-cardiac wall), pericardial (in particular, to define a reference potential, or to apply a shock), or intravascular (the lead, for example, is introduced into the coronary sinus until a site located in front of the wall of the left ventricle).

A first aspect of the development of applications for these devices is the multiplication of the number of electrodes, in particular for the devices known as "multi-site" which make it possible to choose the sites of stimulation/detection in order to optimize the functioning of the device. Thus, in the particular case of the devices for the ventricular re-synchronization (such devices being known as Cardiac Resynchronization Therapy or "CRT" devices), once implanted into the patient a device provided with electrodes allowing to stimulate both ventricles. The stimulation of the right ventricle (and the right atrium) is operated by a traditional intracardiac lead, but for the left ventricle the access is more complex: the stimulation is generally operated by means of a lead introduced into the coronary sinus of the right ventricle and then pushed in a coronary vein on the pericardium, so that the extremity of the lead comes to be placed in front of the left ventricle. This procedure is rather delicate, because the diameter of the coronary vessel is reduced as the lead advances, so that it is not always easy to find the optimal position at the time of the implantation. Moreover, the proximity of the phrenic nerve can sometimes lead to inappropriate stimulations. It is to overcome these difficulties that the development was conducted on leads to obtain what is known as a "multi-electrode" lead, provided with, as an example, ten electrodes and of which it is possible to select after implantation the most effective stimulation electrode.

To manage this multiplicity of electrodes, multiplexing systems were developed allowing the connection of the various electrodes with the two wires traversing the lead and connected at the output of the generator. The U.S. Patent Publication 2003/0149456 A1 (Rottenberg et al.) described a generator connected to a multi-electrode lead by two wires associated with a multiplexer/demultiplexer. These two wires, on the one hand, ensure the sensing of the depolarization signals and the delivery of the stimulation impulses, and, on the other hand, deliver to the multiplexer/demultiplexer the logical signals making it possible to control selection switches for one or more electrodes on the lead. These signals also ensure the supply to the multiplexing/demultiplexing circuit and to the switches the necessary energy for their functioning. The multiplexing/demultiplexing circuits and the switches are preferably located at the extremity of lead, therefore remotely from the generator.

Another aspect of the use of the implantable device is the integration of various sensors within the lead, more particularly of a blood acceleration sensor or a blood pressure sensor, in particular a sensor of the endocardiac acceleration (EA). The signals collected by these sensors allow the control of various functions of the device: in particular, the measurement of the peaks of endocardiac acceleration (PEA) gives representative information of the instantaneous hemodynamic state of the patient.

Documents EP 0515319 A1 and its counterpart U.S. Pat. No. 5,304,208, EP 0582162 A1 and its counterpart U.S. Pat. No. 5,454,838, and EP 0655260 and its counterparts U.S. Pat. No. 5,693,075 and U.S. Pat. No. 5,496,351 (all three in the name of Sorin Biomedica Cardio SpA) describe endocardiac acceleration sensors provided at the distal end of an intracardiac lead, introduced into the myocardium and connected to the pacemaker or a defibrillator case.

The presence of such sensors at the distal extremity of lead requires a specific connection for the transmission of the signals from the sensor to the generator connected at the opposed proximal extremity. This specific connection to the sensor comes in addition to the already existing connections between the generator and the electrodes located at the distal extremity of lead, connections themselves ensured by specific wires, with or without multiplexing.

Lastly, a third aspect of the recent development of the implantable medical devices, in particular in the cardiac field, is the multiplication of the number of leads connected to the same generator. More recently developed devices typically include three different leads, respectively associated with the right ventricle, the left ventricle and the right atrium, each one of these leads itself being provided with several electrodes, and eventually with a sensor at the distal extremity of lead.

The document WO 2006/029090 A2 (Proteus Biomedical, Inc.) proposes a system in which one two-wire bus conveys digital signals of selection/configuration of satellites integrated into the lead, as well as pulses of stimulation and analog sensed signals of the patient. Concern with this system arises with the fact that the coded selection/configuration signals also are delivered to the heart via the electrodes of the lead in the form of salvos of impulses. It is therefore necessary to very carefully calibrate these impulses in order not to start an inappropriate depolarization of cardiac tissue.

OBJECTS AND SUMMARY OF THE INVENTION

It is therefore an object of the present invention is to propose a system able to manage safely, completely, reliably and in an adaptable manner the operation of implantable medical devices implementing leads equipped with a multiplicity of electrodes and/or sensors, and including leads connected to the same generator.

The invention broadly proposes a system that is able to manage globally all the configurations of leads and/or electrodes and/or sensors able to be associated to the same generator, without modification of the hardware components of the generator. The invention proposes an active implantable medical device of a known type, for example, according to the WO 2006/029090 A2 and its counterpart U.S. Pat. No. 7,214,189.

One aspect of the invention is directed to an active implantable medical device, including a generator that has circuits for analyzing physiological signals and/or for producing stimulation impulses and is able to send and receive digital data with at least one lead, connected on its proximal side to the generator. The lead includes at its distal end at least one electrode to contact tissues to deliver stimulation impulses and/or to collect physiological signals; a two-wire connection able to connect the at least one electrode to the generator; at least one transducer of a sensor or an actuator type; and a connection for digital data communication, able to couple at least one transducer to the generator via the two-wire connection. The device further includes a communication circuit that sends and receives digital data inside the generator and produces a control in the direction of the transducer, said control being selected from among a plurality of controls.

The transducer includes a circuit that is able to receive, decode, and carry out the delivered control and send information in response to the reception of a specific control requesting such information. The generator in turn includes a communication circuit that is able to receive and decode that information from the transducer.

Further, the generator circuits are able to produce a control micro-impulse before the sending of said control in the direction of the transducer, said micro-impulse having at least one particular form characteristic, distinctive in comparison to and therefore distinguishable from said stimulation impulse. The lead includes on its distal end controlled switches, selectively interposed between said at least one electrode and said respective wires of the two-wire connection; and a control circuit coupled to the two-wire connection, able:

i) to recognize the aforementioned particular form characteristic among the impulses detected on the two-wire connection, so as to discriminate between an impulse of stimulation and a control micro-impulse; and ii) on detection of a control micro-impulse, to control the opening of the controlled switches so as to insulate the at least one electrode from the two-wire connection, this later being then connected only to the transducer.

Preferably, the particular form characteristic of the control micro-impulse is a characteristic selected from among the group consisting of: a selected duration, a polarity, and an amplitude of the micro-impulse; and more preferably a combination of at least two of the forgoing characteristics. In addition, it is preferred that the control circuit obtains a supply voltage from the impulses detected on the two-wire connection.

The aforementioned controls are preferably controls selected from among the group consisting of: a word (byte of data) of synchronization; a word of identification for the recipient transducer; a closing of the communication; a return to a default configuration of the transducer; a writing of data in a memory of the transducer; and a reading of data from the memory of the transducer.

Further, the information is preferably an information field in a transmission containing information selected from among the group consisting of: a word of synchronization; a word of identification of the transmitting and/or receiving transducer; data contained in a memory of the transducer; an acknowledgment receipt following an action carried out on command of the generator; and a code of detection and correction of error.

In an alternate preferred embodiment, the generator for an active implantable medical device has a receptacle to receive a lead able to be connected on its proximal side to the generator, said lead having at least one electrode, at least one distal transducer, and a two-wire connection able to connect to the generator the at least one electrode, and a connection for digital data communication, able to couple the at least one transducer to the generator via the two-wire connection:

a circuit for analyzing physiological signals and/or producing stimulation impulses; and a circuit for sending and receiving digital data, including:

circuits for producing one or more controls signals to be delivered to the transducer; and circuits for receiving and decoding the information received from the transducer in response to the reception of a specific control among the aforementioned controls;

circuits for producing the control micro-impulse before the sending of said controls signals to the transducer, said micro-impulse having at least a particular form characteristic, distinctive in comparison to the stimulation impulses.

In an alternate preferred embodiment, the lead has a proximal end and a distal end, and includes:

at least one electrode at the distal end able to come in contact with surrounding tissues, to apply stimulation impulses and/or to collect physiological signals; and at least one transducer at the distal end of the sensor or actuator type;

an interface connector for connecting the lead to a generator at the proximal end with a two-wire connection able to connect the at least one electrode to the generator, and a connection for data communication able to couple the transducer to the generator via the two-wire connection, circuits for receiving, decoding and carrying out a controls signals produced by the generator;

circuits for sending data in response to the reception of a specific controls signals;

controlled switches at the distal end having an open condition and a closed condition, interposed between the at least one electrode and the respective wires of the two-wire connection; and a control circuit at the distal side coupled to the two-wire connection and able:

i) to recognize a control micro-impulse having a particular form characteristic among the impulses detected on the two-wire connection, so as to discriminate between impulses of stimulation and control micro-impulses; and ii) on detection of a control micro-impulse, to control the opening of the controlled switches so as to insulate the at least one electrode from the two-wire connection, this later being then connected only to the transducer.

It is another object of the present invention, considered separately, to provide an improved generator as well as the lead for such a device and, as such, a control signal implemented within the device.

BRIEF DESCRIPTION OF THE DRAWINGS

Further features, characteristics and advantages of the present invention will become apparent to a person of ordinary skill in the art in view of the following detailed description of preferred embodiments of the invention, made with reference to the annexed drawings, in which the same numerical references indicate, from one figure to another, identical or functionally similar elements, and in which.

DETAILED DESCRIPTION OF THE INVENTION

Figure 1:
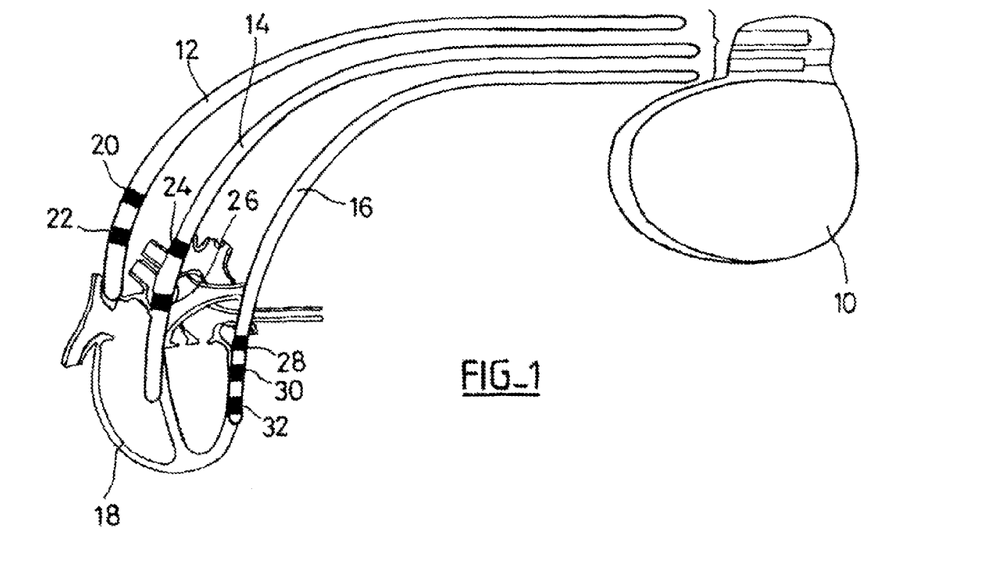
FIG. 1 represents, in a diagrammatic view, an implantable medical device including a generator and three leads intended to be implanted in three respective cavities of a patient's myocardium.

With reference to FIG. 1, a preferred embodiment is shown in which reference 10 indicates the case of the generator which is a device that could be defibrillator, pacemaker or CRT device type. It will be noted that this embodiment of the present invention is not restrictive at all, and that the invention can apply to other types of implants such as devices of detection/stimulation of nerves, muscles, etc.

Generator 10 is associated with three distinct leads 12, 14 and 16 positioned in various sites of myocardium 18. Lead 12 comprises at its distal end two sensors or actuators 20 and 22, for example, an accelerometer 20 and one actuator 22 allowing the selection of an electrode of stimulation (it will be noted that the sensor and the actuator can be located in the same module or not, as deemed appropriate).

The lead 14 comprises at its distal end a sensor 24, for example, an accelerometer, and an actuator 26 allowing the selection of an electrode of stimulation (these elements will be described more in detail below with reference to FIG. 3). Lastly, lead 16 integrates at its distal end three sensors or actuators 28, 30, 32, for example, an accelerometer or a pressure sensor 28 and two actuators 30, 32 allowing the selection of two respective electrodes of stimulation.

Figure 3:
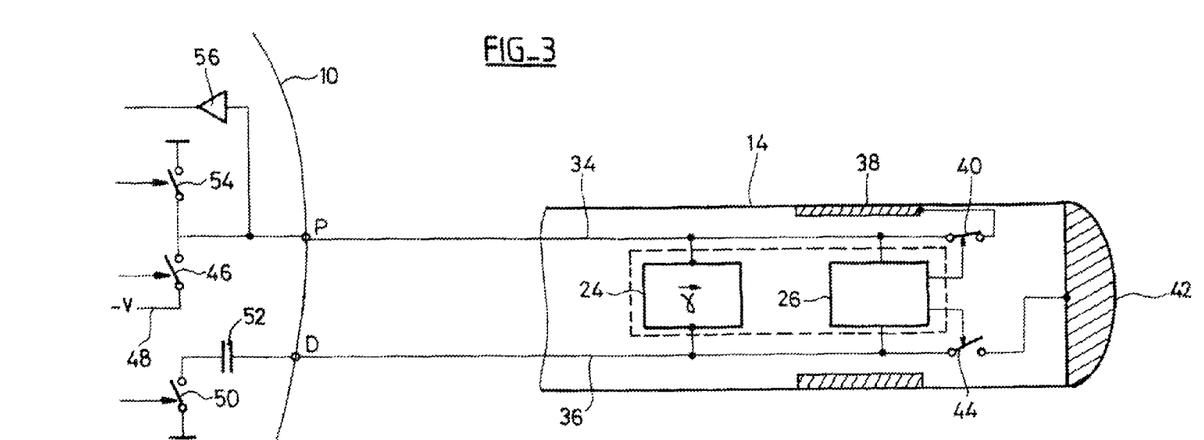
FIG. 3 illustrates, in the form of schematic blocks, the various circuits associated with the connection between the generator and the distal end of the lead, where the electrodes are situated, one actuator and one acceleration sensor.

With reference to FIG. 3, the extremity of the lead 14 is described and illustrated in greater detail. It should be understood that the two other leads 12 and 16 are configured in a similar way.

Lead 14 includes two wires of connection in the form of two micro-cables 34, 36 which extends along its length and are connected to generator 10. These connection wires 34 and 36 will be indicated hereafter as "proximal micro-cable" 34 and "distal micro-cable" 36, and the corresponding terminals of the generator will be indicated "distal" and "proximal," by analogy with the positioning of the two electrodes of an intracardiac bipolar lead.

Micro-cables 34 and 36 are connected to a sensor 24, for example, an acceleration sensor, and to a control circuit 26 of the actuator.

By convenience, for the simplicity of the example illustrated, element 24 is described in the form of a sensor, but the invention is not limited to this type of component: the element 24 can be a sensor (i.e., a signal transducer allowing to produce an electric signal resulting from the variations of a detected physical parameter), but also an active electronic circuit such as amplifier, filter, . . . associated or not to a sensor positioned near this circuit, or an Micro Electro Mechanical Systems (MEMS), or in a general way any technologically integrable active element positioned in the lead, typically at the extremity of a lead.

The proximal micro-cable 34 can be connected to a proximal electrode 38 via a switch 40 controlled by circuit 26, and the distal micro-cable 36 can be connected to a distal electrode 42 via a switch 44 controlled by circuit 26 (the internal structure of which will be described hereafter in more detail with reference to FIG. 4). Switches 40 and 44 can, in a known manner, be produced in the form of a MOS transistors or of Micro Electro Mechanical Systems (MEMS), components technologically integrable on the substrate of a chip which can be incorporated in the body of lead. Such components, for example, are described in U.S. Patent Publication US2004/0220650 A1 to which one skilled in the art may refer.

Generator 10 is provided, in addition to the traditional circuits of sensing/stimulation (not illustrated in as much as they form no part of the present invention), with circuit structures making it possible to read or write data coming from or going to sensor 24 or actuator 26, or of any other sensor or actuator available on the lead.

Figure 2:
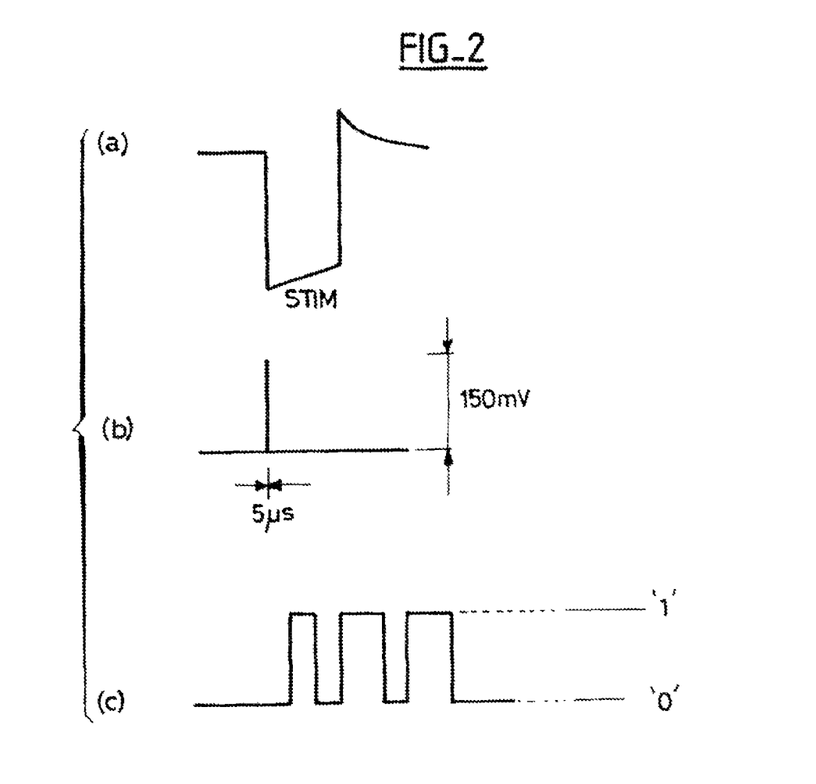
FIG. 2 illustrates various wave forms of impulses traveling along the communication two-wire connection of one the leads.

To generate a logical level "1" as illustrated on the FIG. 2c (by convention, the logical level "1" corresponds to the high level), the generator controls the closing of switch 46 connecting micro-cable 34 to a source of constant voltage 48 (for example −2 V), as well as switch 50 connecting the micro-cable 36 to the reference (e.g., ground) potential via a capacitor 52. Capacitor 52 is an insulating capacitor making it possible to avoid the passage of the continuous voltage; it is foreseen also to have a switching system, not represented, making it possible to discharge capacitor 52 at the proper time. At the same time, the generator 10 opens switch 54 connecting the micro-cable 34 to the reference potential. In an alternative embodiment, it is possible to send positive impulses on micro-cable 36 by switch 50 connected to a positive voltage, by connecting micro-cable 34 at the ground by switch 54. Other variations will occur to a person of ordinary skill in the art.

To generate a low logical level "0", the generator closes switches 50 and 54, and opens switch 46. For the reading of a logical level "0" or "1" (low or high level, respectively) switches 46 and 54 are opened, and switch 50 closed: the reading of the logical level is done then via a reading (sensing) amplifier 56.

Figure 4:
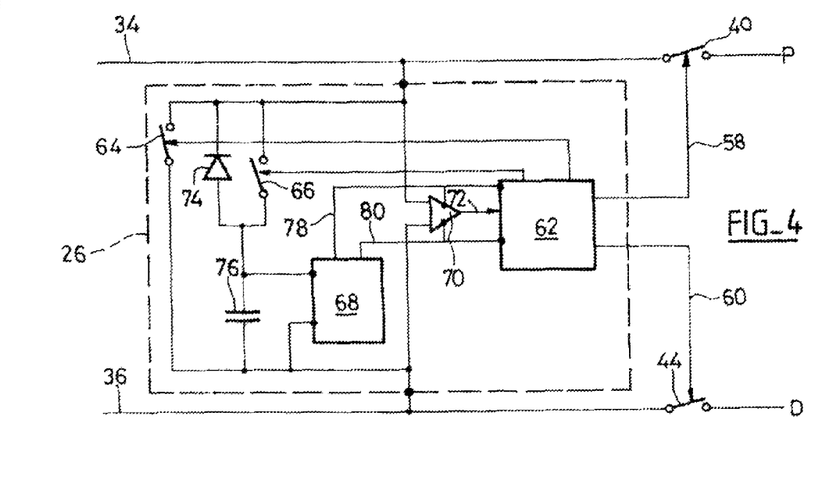
FIG. 4 illustrates a schematic circuit of selected components of the control circuit of the actuator of FIG. 3.

The internal structure of control circuit 26 of the actuator is represented more in detail in FIG. 4. Circuit 26 ensures not only the controlling of switches 40 and 44, via controls 58, 60 produced by a logical circuit 62, but also the generation of logical levels "0" or "1" to the generator 10, so as to allow a bidirectional communication of data not only in the direction generator to actuator, but also in return in the direction actuator to generator. To generate a logical level "0", circuit 26 closes a switch 64 putting in direct connection the two micro-cables 34 and 36; the switch 66, which role will be described below, is then in an open state (in the alternative embodiment mentioned above, switch 50 would be closed, and switches 54 and 46 open). To generate a logical level "1", circuit 26 opens switch 64 and closes switch 66 making it possible to apply to micro-cable 34 a continuous fixed voltage generated by a circuit 68. Switches 64 and 66 are controlled by logic circuit 62.

To put the lead in a configuration authorizing the exchange of data, the generator 10 produces a micro-impulse applied between micro-cables 34 and 36. This micro-impulse, represented on the FIG. 2b, presents a duration, a polarity and/or a specific amplitude, discriminating in relation to the other signals likely to be present on micro-cables 34 and 36, for example, signals of stimulation (such as those illustrated FIG. 2a) or injection of current for a bio-impedance measurement. This micro-impulse lasts for example 5 µs with an amplitude of 150 mV. A comparator 70, whose two inputs are connected respectively to micro-cables 34 and 36, detects this particular form and informs logic circuit 62 by signal 72. The logic circuit 62 then generates the signals 58 and 60 which control the opening of switches 40 and 44.

It will be noted that comparator 70 plays a double role: in addition to the detection of a specific impulse for the controlling of switches 40 and 44, it also ensures the detection of the logical levels "0" or "1" sent by generator 10 in direction of logic circuit 62.

To function, circuit 26 requires a power supply. Power is brought by the logical signals traveling on micro-cables 34 and 36, such as those of the FIG. 2c described above. To ensure the continuity of this power supply, a diode 74 charges a capacitor 76 when the voltage on micro-cable 36 is higher than the voltage on micro-cable 34. Capacitor 76 stores the load and feeds circuit 68, which includes a voltage multiplier making it possible to generate voltages 78 and 80 being used to supply comparator 58 and the logic circuit 62. The charging of capacitor 76 takes place when, on the generator side, switches 46 and 50 are closed and switch 54 is open, and on the actuator side, switches 64 and 66 are open. The discharge of capacitor 52 takes place when, on the generator side, switches 50 and 54 are closed and switch 40 is open, and, on the actuator side, switch 64 is closed and switch 66 open. The power supply of any other sensor or actuator present on the lead can be carried out on the same manner.

Figure 5:
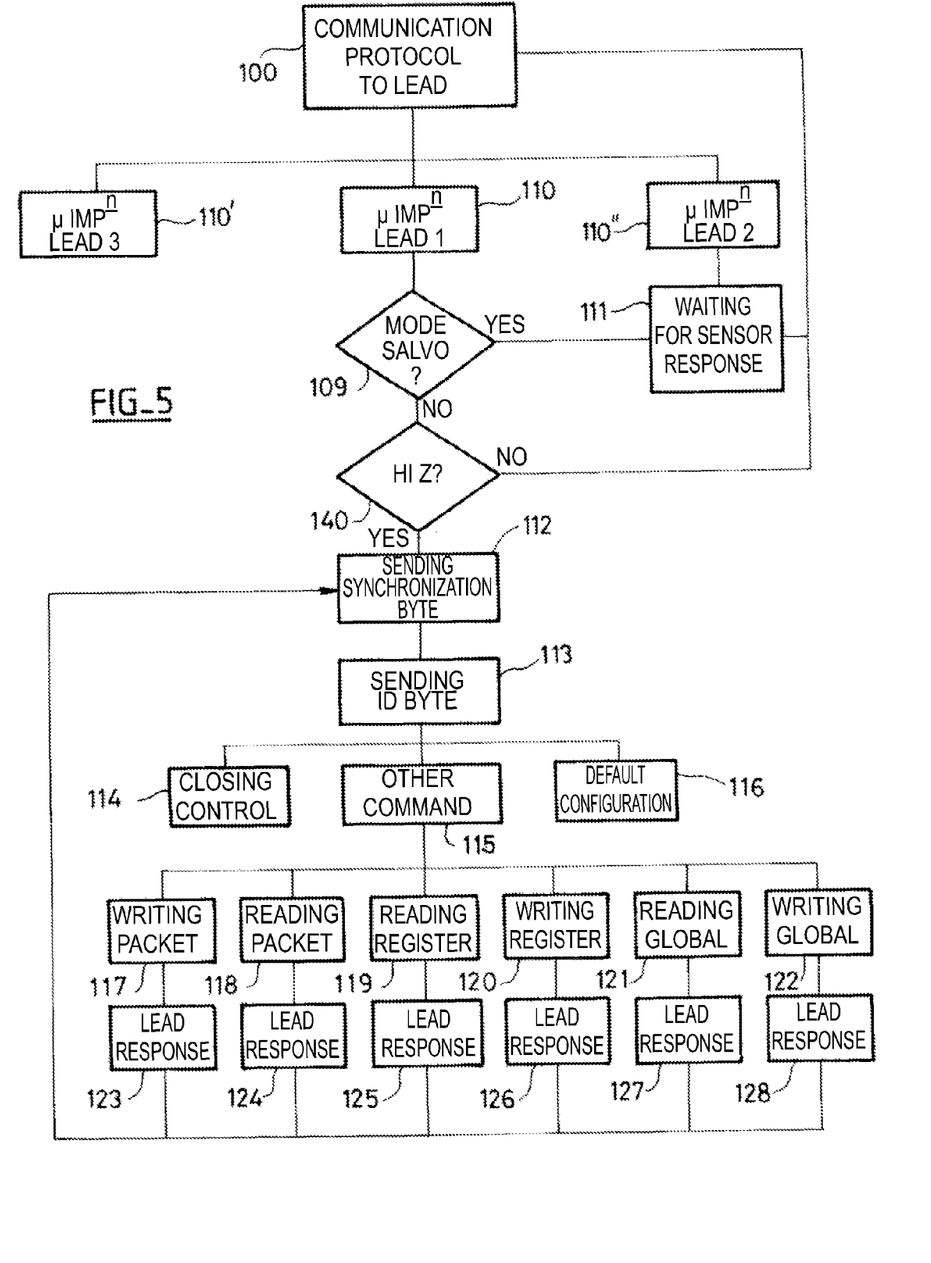
FIG. 5 is a flow chart illustrating the various steps of the communication protocol, seen from the generator side.
Figure 6:
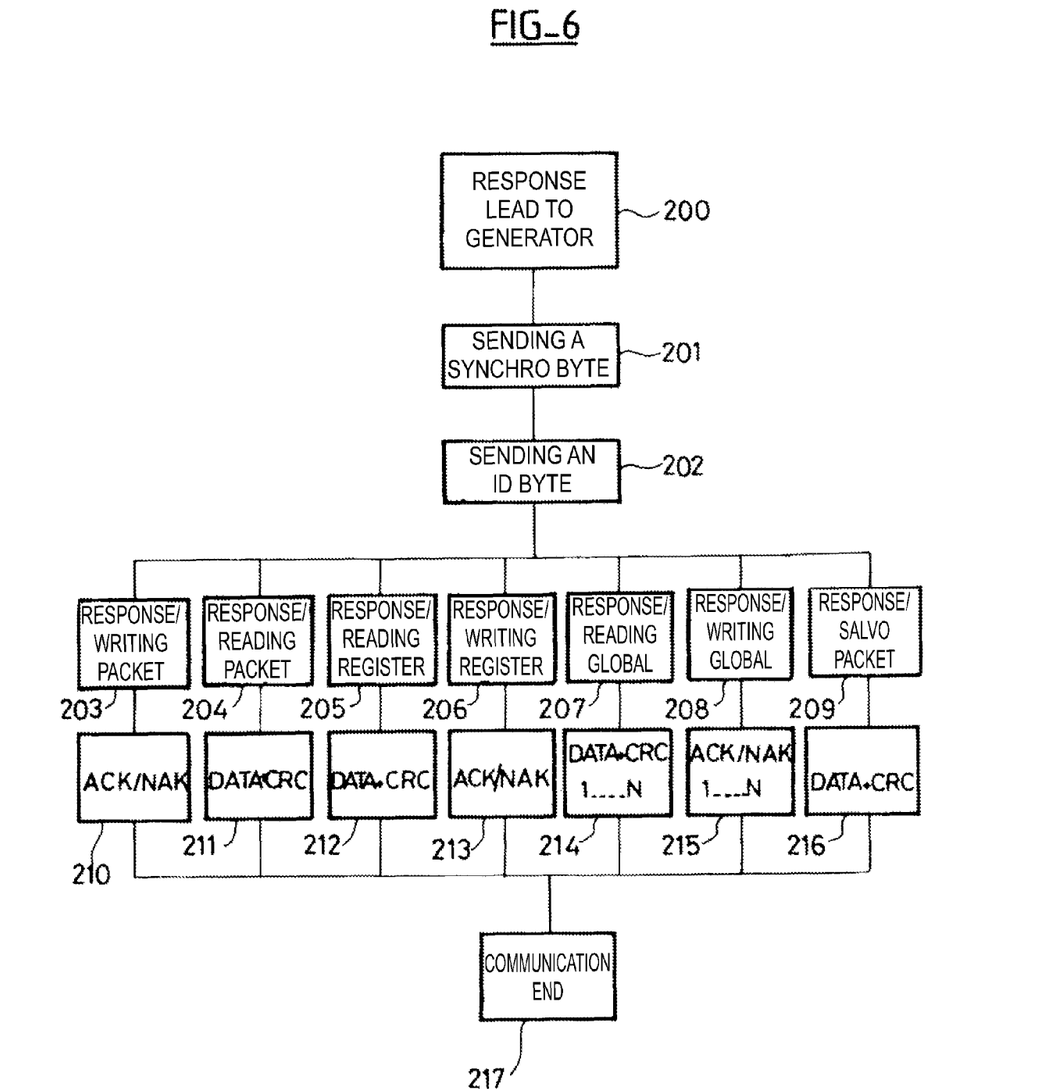
FIG. 6 is a flow chart illustrating the various steps of the communication protocol, seen from the lead side.

Now we will describe, with reference to FIGS. 5 and 6, the communication protocol between the generator and the various sensors and actuators (or other similar active elements) integrated into the various leads connected to this generator. FIG. 5 illustrates this protocol seen from the generator side, while FIG. 6 illustrates this same protocol seen from the lead side.

The initial state is that corresponding to block 100 (FIG. 5), with generator 10 of FIG. 1 connected to a plurality of leads 12, 14, 16... carrying themselves a plurality of sensors and/or actuators 20, 22 ... 30, 32 .... Each sensor or actuator contains a register with digital data, intended to be programmed, read and/or written remotely from generator 10.

In the communication protocol, generator 10 is the Master. It can decide to program, read or write simultaneously the registers of one or several leads 12, 14 or 16.

The selection of a lead is done by the sending of a micro-impulse (blocks 110, 110' or 110"), as it was described previously and illustrated in reference to the FIG. 2b. The detection of such a micro-impulse by the sensors and actuators of the lead provokes the control switches to disconnect the electrodes from the associated to the micro-cables within the lead. In the example of FIGS. 3 and 4, this micro-impulse is detected by the circuit 70 which, via the logic circuit 62, controls the opening of switches 40 and 44, which in turn causes to isolate the distal electrode 42 and proximal electrode 38 from the respective micro-cables 36 and 34, which in turn are only connected to the sensor 24 and actuator 26.

Advantageously, the generator can function according to an optional mode called "salvo mode." This means that, for example, every 8 ms the sensor 24 sends to the generator the recorded data accumulated during the last 8 ms. In such a case, the generator awaits a response from the sensor of the lead (block 111), this response corresponding to the sequence of blocks 201, 209, 216 and 217 (FIG. 6) with successively: sending a synchronization word (byte) (block 201); sending an identification word (byte) of the register in which the data to be transmitted by the sensor (block 202) are contained; sending a code indicating that the response is a response of the type of data packet, specific in the mode salvo (block 209); sending the data themselves and sending a checking and correction of error code (code CRC) allowing to secure the transmission (block 216); end of the communication (block 217).

It will be noted that, here and in the following detailed description, the controls can exist without comprising a synchronization word, for example, if one uses a width modulation of impulses of which the duration is sufficiently large to tolerate desynchronized clocks, and whose width determines the logical level. The synchronization word can in addition include a coded preamble which makes it possible to test the synchronization of the clocks. In addition, the words can use the known "Manchester" encoding.

Lastly, the identification word makes it possible to identify not only the register, but also the transducer and the lead: the identification of the lead is indeed necessary to avoid, by cross talk, the programming of another lead provided with actuators.

If the generator is not in salvo mode (tested at block 109), it checks by a impedance measurement (FIG. 5 element "HiZ" at block 140) that the sensors and actuator are well disconnected from the electrodes. This measurement is operated, in a traditional way, by injection of a current and measurement of the resulting voltage between the two micro-cables. If, by detecting a high impedance value, this measurement confirms the effective disconnection of the electrodes, then the generator sends on the two-wire connection a synchronization byte (block 112) in order to allow the synchronization of the generator clocks with the actuator and the sensors of the selected lead.

The generator sends then a byte of identification (block 113), followed by one of the three following instructions:
  end of the communication and closing of the connection switches to the electrodes, with the sending of a CRC code to secure the transmission (block 114);
  return of all the actuator and sensors to a default configuration, with a CRC code to secure the transmission (block 116);
  another control to come (block 115).
The following controls might follow:
  writing a packet of bytes starting from a given address on one of the actuators or sensors of a lead (block 117);
  reading a packet of bytes starting from an address given on one of the actuators or sensors of a lead (block 118);
  reading a register at a given address on one of the actuator or sensors of a lead (block 119);
  writing a register at a given address on one of the actuator or sensors of a lead (block 120);
  reading a register at a given address on all the actuator and sensors of the same lead (block 121);
  writing a register at a given address on all the actuator and sensors of the same lead (block 122).
All these controls are followed with a CRC code in order to secure the transmission. The generator then waits for the response of the lead (blocks 123 to 128, following respectively blocks 117 to 122). The response, on the leads side, to the controls 117 to 122 is schematized by blocks 203 to 207 on FIG. 6. According to the cases, the response of the lead can take several forms (blocks 210 to 215, respectively):
  ACK: code indicating a correct reception of the control emitted by the generator;
  NAK: code indicating that this reception is erroneous;

DATA+CRC: sending of the requested data, followed with a check code CRC;

ACK/NAK 1 . . . N: each actuator or sensor of the lead answers sequentially by a ACK/NAK, in a given order;

DATA+CRC 1 . . . N: each actuator or sensor of the lead responses sequentially by providing the requested data DATA, followed by an associated check code CRC, in a given order.

The communication then ends (block 217). In any event, if a micro-impulse, produced by the generator to open the switches of the actuator, is not followed in a given time period (for example, 100 µs) by another signal received on the generator, the switches are again closed to allow a return to the configuration by default, so as to be able to ensure with certainty the sensing of signals of the cardiac depolarization and/or the application of signals of stimulation or defibrillation.

A person skilled in the art will appreciate that the present invention can be practiced by other than the described embodiments, which are presented for purposes of illustration and not of limitation.

We claim:

1. An active implantable medical device, comprising:
a generator, having:
   means for analyzing physiological signals and/or for producing stimulation impulses; and
   means for sending and receiving digital data, including means for producing a control in the direction of the transducer, said control being selected from among a plurality of controls, and means for receiving and decoding an information, and
at least one lead having a proximal end and a distal end, connected on the proximal end to the generator and comprising at the distal end:
   at least one electrode able to contact surrounding tissues to apply said stimulation impulses and collect said physiological signals;
   a two-wire connection able to connect the at least one electrode to the generator; and
   at least one transducer of a sensor or an actuator type including means for receiving, decoding, and carrying out said control, means for sending an information to said generator in response to the reception of a specific control, and a memory; and
   a connection for digital data communication, able to couple said at least one transducer to the generator via the two-wire connection;
Wherein said:
   generator further comprising means for producing a control micro-impulse before the sending of said control to the transducer, said micro-impulse comprising at least one particular characteristic form, distinctive from said stimulation impulses; and
   the lead further comprises on the distal end:
      controlled switches, selectively interposed between said at least one electrode and said respective wires of the two-wire connection; and
      a control circuit coupled to the two-wire connection, able:
         i) to recognize said particular form characteristic detected on the two-wire connection, so as to discriminate between impulses of stimulation and control micro-impulses; and
         ii) on detection of a control micro-impulse, to control the opening of the controlled switches so as to insulate the at least one electrode from the two-wire connection, and connect the transducer to said two-wire connection; and
         iii) wherein the particular form characteristic of said control micro-impulse is discriminating from a logic level 1 signal and a logic level 0 signal on the two-wire connection.

2. The device of claim 1, wherein said particular form characteristic of the control micro-impulse is a characteristic selected from among the group consisting of: a micro-impulse duration; a micro-impulse polarity; a micro-impulse amplitude; and a combination of at least two of said foregoing characteristics.

3. The device of claim 1, wherein the control circuit further comprises means for producing a supply voltage from the impulses detected on the two-wire connection.

4. The device of claim 1, wherein the said controls are selected from among the group consisting of: a synchronization word; a word of identification for a recipient transducer; a closing of the communication; a return to a default configuration of a transducer; a writing of data in a memory of a transducer; and a reading of data from a memory of a transducer.

5. The device of claim 1, wherein said information is selected from among the group consisting of: a synchronization word; a word of identification of a transmitting and/or a receiving transducer; a data contained in a transducer memory; an acknowledgment receipt following an action carried out on command of the generator; and a code of detection and correction of error.

6. A generator for an active implantable medical device comprising:
   a receptacle to receive and connect to a proximal end of a lead, said lead having at least one electrode, at least one distal transducer, and a two-wire connection able to connect to the generator said at least one electrode, and a connection for digital data communication, able to couple said at least one transducer to the generator via the two-wire connection;
   means for analyzing physiological signals and/or producing stimulation impulses; and
   means for sending and receiving digital data, including:
      means for producing and delivering a control to the transducer; and
      means for receiving and decoding an information received from the transducer in response to said delivered control; and
      means for producing a control micro-impulse to be delivered before the sending of said control to the transducer, said micro-impulse having at least one particular form characteristic, distinctive from a stimulation impulse; and
      wherein the particular form characteristic of said control micro-impulse is discriminating from a logic level 1 signal and a logic level 0 signal on the two-wire connection.

7. The device of claim 6 wherein the control further comprises a control selected from among the group consisting of: a word of synchronization; a word of identification from a transmitting and/or receiving transducer; a closing of the communication; a return to a default configuration of the transducer; a writing of data in a memory of the transducer; and a reading of data from a memory of the transducer.

8. The device of claim 6 wherein the information further comprises a field of information, including at least one information selected from among the group consisting of: a word of synchronization; a word of identification of a transmitting and/or receiving transducer; a data contained in a memory of a transducer; an acknowledgment receipt following an action carried out on command of the generator; and a code of detection and correction of error.

9. A lead for an active implantable medical device having a proximal end and a distal end, comprising:
at least one electrode at the distal end able to come in contact with tissues, to apply a stimulation impulse and to collect a physiological signal; and at least one transducer at the distal end of the sensor or actuator type;
connecting means for connecting to a generator at the proximal end able to be connected to the lead, with a two-wire connection to connect the at least one electrode to the generator, and a connection for data communication able to couple the transducer to the generator via the two-wire connection,
means for receiving, decoding and carrying out a control received from the generator; and
means for sending an information to said generator in response to the reception of a specific control;
controlled switches at the distal end having an open condition and a closed condition, selectively, interposed between the at least one electrode and the respective wires of the two-wire connection; and
a control circuit at the distal side coupled to the two-wire connection and able:
  i) to recognize a control micro-impulse having a particular form characteristic among the impulses detected on the two-wire connection, so as to discriminate between impulses of stimulation and control micro-impulse; and
  ii) on detection of a control micro-impulse, to control the opening of the controlled switches so as to insulate the at least one electrode from the two-wire connection, and connect the transducer to the two-wire connection; and
  iii) wherein the particular form characteristic of said control micro-impulse is discriminating from a logic level 1 signal and a logic level 0 signal on the two-wire connection.

10. The device of claim 9, wherein said control is selected from among the group consisting of: a word of synchronization; a word of identification from a transmitting and/or receiving transducer; a closing of the communication; a return to a default configuration of a transducer; a writing of data in a memory of a transducer; and a reading of data for a memory of a transducer.

11. The device of claim 9, wherein said information further comprises a field of information, including at least one information selected from among the group consisting of: a word of synchronization; a word of identification of the transmitting and/or receiving transducer; data contained in a memory of the transducer; an acknowledgment receipt following an action carried out on command of the generator; and a code of detection and correction of error.

* * * * *